United States Patent
Feucht et al.

(10) Patent No.: US 6,967,188 B2
(45) Date of Patent: Nov. 22, 2005

(54) SELECTIVE HETEROARYLOXY-ACETAMIDES-BASED HERBICIDES

(75) Inventors: Dieter Feucht, Monheim (DE); Peter Dahmen, Neuss (DE); Mark Wilhelm Drewes, Langenfeld (DE); Rolf Pontzen, Leichlingen (DE); Mathias Kremer, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 102 days.

(21) Appl. No.: 10/296,006

(22) PCT Filed: May 9, 2001

(86) PCT No.: PCT/EP01/05242

§ 371 (c)(1),
(2), (4) Date: Nov. 20, 2002

(87) PCT Pub. No.: WO01/89301

PCT Pub. Date: Nov. 29, 2001

(65) Prior Publication Data

US 2004/0102321 A1 May 27, 2004

(30) Foreign Application Priority Data

May 22, 2000 (DE) .......................... 100 25 306
Aug. 24, 2000 (DE) .......................... 100 41 619

(51) Int. Cl.$^7$ ................... A01N 33/22; A01N 43/54; A01N 43/90; A01N 43/824; A01N 47/36
(52) U.S. Cl. ................... 504/134; 504/136; 504/139; 504/263
(58) Field of Search ................... 504/134, 136, 504/139, 263

(56) References Cited

U.S. PATENT DOCUMENTS

| | | | |
|---|---|---|---|
| 4,408,055 A | 10/1983 | Forster et al. | 548/125 |
| 4,509,971 A | 4/1985 | Förster et al. | 71/90 |
| 4,540,430 A | 9/1985 | Förster et al. | 71/90 |
| 4,549,899 A | 10/1985 | Förster et al. | 71/90 |
| 4,585,471 A | 4/1986 | Förster et al. | 71/90 |
| 4,645,525 A | 2/1987 | Förster et al. | 71/88 |
| 4,756,741 A | 7/1988 | Förster et al. | 71/90 |
| 4,784,682 A | 11/1988 | Förster et al. | 71/88 |
| 4,788,291 A | 11/1988 | Förster et al. | 548/187 |
| 4,833,243 A | 5/1989 | Förster et al. | 540/480 |
| 4,929,743 A | 5/1990 | Förster et al. | 548/187 |
| 4,988,380 A | 1/1991 | Förster et al. | 71/90 |
| 5,090,991 A | 2/1992 | Förster et al. | 71/90 |
| 5,494,886 A | 2/1996 | Kehne et al. | 504/215 |
| 5,811,373 A | 9/1998 | Santel et al. | 504/139 |
| 5,858,920 A | 1/1999 | Dahmen et al. | 504/103 |
| 5,912,206 A | 6/1999 | Deege et al. | 504/138 |
| 5,945,379 A | 8/1999 | Dollinger et al. | 504/130 |
| 5,985,797 A | 11/1999 | Dahmen et al. | 504/130 |
| 5,990,044 A | 11/1999 | Santel et al. | 504/128 |
| 6,001,774 A | 12/1999 | Mito | 504/130 |
| 6,174,838 B1 | 1/2001 | Dahmen et al. | 504/139 |
| 6,492,301 B1 | 12/2002 | Hacker et al. | 504/128 |

FOREIGN PATENT DOCUMENTS

FR 2 564 288 5/1985

OTHER PUBLICATIONS

Weeds, (month unavailable) 1967, pp. 20–22, Calculating Synergistic and Antagonistic Responses of Herbicide Combinations by S. R. Colby.

*Primary Examiner*—S. Mark Clardy
(74) *Attorney, Agent, or Firm*—Richard E.L. Henderson

(57) ABSTRACT

The invention relates to novel herbicidal synergistic active compound combinations comprising heteroaryloxyacetamides and known herbicidally active compounds and/or safeners described in the description and their use for the selective control of weeds in crops of various useful plants.

9 Claims, No Drawings

SELECTIVE HETEROARYLOXY-ACETAMIDES-BASED HERBICIDES

The invention relates to novel selective-herbicidal synergistic active compound combinations comprising known heteroaryloxy-acetamides and known herbicidally active compounds and/or compounds which improve crop plant tolerance, which active compound combinations can be used with particularly good results for the selective control of weeds in crops of various useful plants.

As strong herbicides, which are active in particular against monocotyledonous weeds, heteroaryloxy-acetamides have been the subject of a number of patent applications (cf. EP-A 5501, EP-A 18497, EP-A 29171, EP-A 94514, EP-A 100044, EP-A 100045, EP-A 161602, EP-A 195237, EP-A 348734, EP-A 348737, DE-A 4317323). However, the activity of these compounds and/or their compatibility with crop plants is/are not always entirely satisfactory.

Furthermore, active compound combinations of heteroaryloxy-acetamides and other herbicidally active compounds for obtaining a synergistic effect (cf. WO-A 94/02014, WO-A-96/07323, WO-A-96/11575, WO-A-96/17519, WO-A-98/08383, cf. also U.S. Pat. No. 5,858,920, U.S. Pat. No. 5,945,379, U.S. Pat. No. 5,985,797) or of heteroaryloxy-acetamides and compounds which can improve the crop plant tolerance of herbicides (cf. DE-A 3418167, cf. also U.S. Pat. No. 5,858,920) have been disclosed. However, the use properties of these combination products are likewise not always entirely satisfactory.

Surprisingly, it has now been found that a number of known active compounds from the group of the heteroaryloxy-acetamides, when used together with known herbicidally active compounds from various substance classes and/or compounds which improve crop plant tolerance, show pronounced synergistic effects with respect to the action against weeds and/or have significantly improved crop plant tolerance and can be used particularly advantageously as broad-spectrum combination preparations for the selective control of weeds in crops of useful plants, such as, for example, in cotton, barley, maize, potatoes, oilseed rape, rice, soya beans, sunflowers, wheat and sugar cane.

The invention provides selective herbicidal compositions, characterized in that they comprise an effective amount of an active compound combination consisting of (a) a heteroaryloxy-acetamide of the general formula (I)

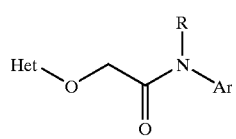

(I)

in which

Ar represents optionally halogen-, $C_1$–$C_4$-alkyl- or $C_1$–$C_4$-halogenoalkyl-substituted phenyl, Het represents thiadiazolyl, which is substituted by halogen or by in each case optionally halogen-substituted $C_1$–$C_4$-alkyl or phenyl, and R represents alkyl, alkenyl or alkinyl having in each case up to 4 carbon atoms, ("active compounds of group 1") and (b) one or more compounds from a second group of herbicides containing the active compounds mentioned hereinbelow:

1H-1,2,4-triazol-3-amine (amitrole), 2-[2,4-dichloro-5-(2-propinyloxy)-phenyl]-5,6,7,8-tetrahydro-1,2,4-triazolo-[4,3-a]-pyridin-3(2H)-one (azafenidin), N-(4,6-dimethoxy-pyrimidin-2-yl)-N'-[1-methyl-4-(2-methyl-2H-tetrazol-5-yl)-1H-pyrazol-5-ylsulphonyl] urea (azimsulfuron), N-benzyl-2-(4-fluoro-3-trifluoromethyl-phenoxy)-butanamide (beflubutamid), N-butyl-N-ethyl-2,6-dinitro-4-trifluoromethyl-benzeneamine (benfluralin), methyl 2-[2-[4-(3,6-dihydro-3-methyl-2,6-dioxo-4-trifluoromethyl-1(2H)-pyrimidinylphenoxymethyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), 2-[1-[(3-chloro-2-propenyl)-oxy-imino]-propyl]-3-hydroxy-5-(tetrahydro-2H-pyran-4-yl)-2-cyclohexen-1-one (caloxydim, tepraloxydim), ethyl 2-chloro-3-[2-chloro-5-(1,3,4,5,6,7-hexahydro-1,3-dioxo-2H-isoindol-2-yl)-phenyl]-2-propanoate (cinidon-ethyl), 2-[1-[2-(4-chloro-phenoxy)]-propoxyaminobutyl]-5-(tetrahydro-2H-thiopyran-3-yl)-1,3-cyclohexanedione (clefoxydim), (E,E)-(+)-2-[1-[[(3-chloro-2-propenyl)-oxy]-imino]-propyl]-3-hydroxy-2-cyclohexen-1-one (clethodim), methyl 3-chloro-2-[[(5-ethoxy-7-fluoro[1,2,4]triazolo[1,5-c] pyrimidin-2-yl)sulphonyl]amino]-benzoate (cloransulam-methyl), 2-(1-ethoximinobutyl)-3-hydroxy-5-(tetrahydro-2H-thiopyran-3-yl)-2-cyclohexen-1-one (cycloxydim), N-(2,6-dichloro-phenyl)-5-ethoxy-7-fluoro-[1,2,4]-triazolo-[1,5-c]-pyrimidine-2-sulphonamide (diclosulam), 2-[1-[(3,5-difluoro-phenyl)-amino-carbonyl-hydrazono]-ethyl]-pyridine-3-carboxylic acid (diflufenzopyr), (S)-2-chloro-N-(2,4-dimethyl-3-thienyl)-N-(2-methoxy-1-methyl-ethyl)-acetamide (dimethenamid-P), 2-[2-(3-chloro-phenyl)-oxiranylmethyl]-2-ethyl-1H-indene-1,3(2H)-dione (epropodan), (R)-ethyl 2-[4-(6-chloro-benzoxazol-2-yl-oxy)-phenoxy]-propanoate (fenoxaprop-P-ethyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop-P-butyl), the sodium salt of 4,5-dihydro-3-methoxy-4-methyl-5-oxo-N-[(2-trifluoromethoxy-phenyl)-sulphonyl]-1H-1,2,4-triazole-1-carboxamide (flucarbazone-sodium), ethyl [2-chloro-4-fluoro-5-(5-methyl-6-oxo-4-trifluoromethyl-1(6H)-pyridazinyl)-phenoxy]-acetate (flufenpyr), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), the sodium salt of N-(4,6-dimethoxy-pyrimidin-2-yl)-N'-(3-methoxycarbonyl-6-trifluoromethyl-pyridin-2-yl-sulphonyl)-urea (flupyrsulfuron-methyl-sodium), 2-[[[[(4,6-dimethoxy-2-pyrimidinyl)-amino]-carbonyl]-amino]-sulphonyl]-4-formylamino-N,N-dimethyl-benzamide (foramsulfuron), (R)-2-[4-(3-chloro-5-trifluoromethyl-pyridin-2-yl-oxy)-phenoxy]-propanoic acid (and its methyl, -2-ethoxy-ethyl and butyl esters) (haloxyfop, -methyl, -P-methyl, -ethoxyethyl, -butyl), 2-[4,5-dihydro-4-methyl-4-(1-methylethyl)-5-oxo-1H-imidazol-2-yl]-5-

(methoxymethyl)-3-pyridinecarboxylic acid (imazamox), the sodium salt of N-(4-methoxy-6-methyl-1,3,5-triazin-2-yl)-N'-(5-iodo-2-methoxycarbonyl-phenylsulphonyl)-urea (iodosulfuron-methyl-sodium), (4-chloro-2-methylsulphonyl-phenyl)-(5-cyclopropyl-isoxazol-4-yl)-methanone (isoxachlortole), methyl 2-[[[[(4,6-dimethoxy-2-pyrimidinyl)-amino]-carbonyl]-amino]-sulphonyl]-4-[[(methylsulphonyl)-amino]-methyl]-benzoate (mesosulfuron), 2-(4-methylsulphonyl-2-nitro-benzoyl)-1,3-cyclohexanedione (mesotrione), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethyl-benzene (oxyfluorfen), 2-(2,2-difluoroethoxy)-N-(5,8-dimethoxy[1,2,4] triazolo[1,5-c]pyrimidin-2-yl)-6-trifluoromethylbenzenesulphonamide (penoxsulam), 2-chloro-N-(2-ethoxyethyl)-N-(2-methyl-1-phenyl-1-propenyl)-acetamide (pethoxamid), the sodium salt of methyl 2-[[[(4,5-dihydro-4-methyl-5-oxo-3-propoxy-1H-1,2,4-triazol-1-yl)-carbonyl]-amino]-sulphonyl]-benzoate (procarbazone-sodium), 1-chloro-N-[2-chloro-4-fluoro-5-[(6S,7aR)-6-fluoro-tetrahydro-1,3-dioxo-1H-pyrrolo[1,2-c]imidazol-2(3H)-yl]-phenyl]-methanesulphonamide (profluazol), (R)-[2-[[(1-methyl-ethylidene)-amino]-oxy]-ethyl] 2-[4-(6-chloro-2-quinoxalinyloxy)-phenoxy]-propanoate (propaquizafop), 2-chloro-N-(2-ethyl-6-methyl-phenyl)-N-[(1-methyl-ethoxy)-methyl]-acetamide (propisochlor), 1-(3-chloro-4,5,6,7-tetrahydropyrazolo [1,5-a]pyridin-2-yl)-5-(methyl-2-propinylamino)-1H-pyrazol-4-carbonitrile (pyraclonil), ethyl [2-chloro-5-(4-chloro-5-difluoromethoxy-1-methyl-1H-pyrazol-3-yl)-4-fluoro-phenoxy]-acetate (pyraflufen-ethyl), 6-chloro-3-phenyl-pyridazin-4-ol (pyridatol), 7-[(4,6-dimethoxy-2-pyrimidinyl)-thio]-3-methyl-1(3H)-isobenzofuranone (pyriftalide), methyl 2-(4,6-dimethoxy-pyrimidin-2-yl-oxy)-benzoate (pyriminobac-methyl), the sodium salt of 2-chloro-6-(4,6-dimethoxy-pyrimidin-2-ylthio)-benzoate (pyrithiobac-sodium), 3,7-dichloro-quinoline-8-carboxylic acid (quinchlorac), (R)-2-[4-(6-chloro-2-quinoxalinyloxy)-phenoxy]-propanoic acid (and its ethyl and tetrahydro-2-furanyl-methyl esters) (quizalofop-P-ethyl, -P-tefuryl), methyl 2-difluoromethyl-5-(4,5-dihydro-thiazol-2-yl)-4-(2-methyl-propyl)-6-trifluoromethyl-pyridine-3-carboxylate (thiazopyr), (3,5,6-trichloro)-pyridin-2-yl-oxyacetic acid (triclopyr), the sodium salt of N-[[(4,6-dimethoxy-2-pyrimidinyl)-amino]-carbonyl]-3-(2,2,2-trifluoro-ethoxy)-2-pyridinesulphonamide (trifloxysulfuron), N-[4-dimethylamino-6-(2,2,2-trifluoro-ethoxy)-1,3,5-triazin-2-yl]-N'-(2-methoxycarbonyl-phenylsulphonyl)-urea (triflusulfuron-methyl), N-[[(4,6-dimethoxy-2-pyrimidinyl)-amino]-carbonyl]-3-(N-methyl-N-methylsulphonyl-amino])-2-pyridinesulphonamide (cf. WO-A-92/10660), ("active compounds of group 2"),
and, if appropriate, additionally
(c) a compound which improves crop plant tolerance, from amongst the following group of compounds:
4-dichloroacetyl-1-oxa-4-aza-spiro[4.5]-decane (AD-67), 1-dichloroacetylhexahydro-3,3,8a-trimethylpyrrolo[1, 2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinoline-8-oxy-acetate (cloquintocet-mexyl), α-(cyanomethoximino)-phenylacetonitrile (cyometrinil), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), N-(4-methylphenyl)-N'-(1-methyl-1-phenyl-ethyl)-urea (dymron), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), diethyl-1-(2, 4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalenedicarboxylic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), methyl 1-(2-chloro-phenyl)-5-phenyl-1H-pyrazole-3-carboxylate and N-(2-methoxy-benzoyl)-4-[(methylamino-carbonyl)-amino]-benzenesulphonamide ("active compounds of group 3").

Preferred meanings of the radicals listed in the formula (I) shown above are illustrated below.

Ar preferably represents optionally fluorine-, chlorine-, bromine-, methyl-, ethyl- or trifluoromethyl-substituted phenyl.

Het preferably represents 1,2,4-thiadiazolyl or 1,3,4-thiadiazolyl which is substituted by fluorine, chlorine, bromine or by in each case optionally fluorine- and/or chlorine-substituted methyl, ethyl, n- or i-propyl or phenyl.

R preferably represents methyl, ethyl, n- or i-propyl, n-, i-, s- or t-butyl, 2-propenyl, 1-methyl-2-propenyl, 2-butenyl, 2-propinyl, 1-methyl-2-propinyl, 2-butinyl.

Ar particularly preferably represents optionally fluorine-, chlorine-, bromine-, methyl- or trifluoromethyl-substituted phenyl.

Het particularly preferably represents 1,2,4-thiadiazolyl or 1,3,4-thiadiazolyl which is substituted by fluorine, chlorine, bromine or by in each case optionally fluorine- and/or chlorine-substituted methyl, ethyl or phenyl.

R particularly preferably represents methyl, ethyl, n- or i-propyl, n-, i-, s- or t-butyl, 2-propenyl, 1-methyl-2-propenyl, 2-butenyl, 2-propinyl, 1-methyl-2-propinyl, 2-butinyl.

Ar very particularly preferably represents optionally fluorine- or chlorine-substituted phenyl.

Het very particularly preferably represents 1,3,4-thiadiazolyl which is substituted by chlorine, bromine or by fluorine- and/or chlorine-substituted methyl.

R very particularly preferably represents methyl, ethyl, n- or i-propyl, n-, i-, s- or t-butyl.

Examples of compounds of the formula (I) to be used as mixing partners according to the invention are:
N-i-propyl-N-phenyl-α-(5-trifluoromethyl-1,3,4-thiadiazol-2-yl-oxy)-acetamide, N-i-propyl-N-(2-chloro-phenyl)-α-(5-trifluoromethyl-1,3,4-thiadiazol-2-yl-oxy)- acetamide, N-i-propyl-N-(3-chloro-phenyl)-α-(5-trifluoromethyl-1,3,4-thiadiazol-2-yl-oxy)-acetamide, N-i-propyl-N-(4-chloro-phenyl)-α-(5-trifluoromethyl-1,3,4-thiadiazol-2-yl-oxy)-acetamide, N-i-propyl-N-(2-fluoro-phenyl)-α-(5-trifluoromethyl-1,3,4-thiadiazol-2-yl-oxy)-acetamide, N-i-propyl-N-(3-fluoro-phenyl)-α-(5-trifluoromethyl-1,3,4-thiadiazol-2-yl-oxy)-acetamide, N-i-propyl-N-(4-fluoro-phenyl)-α-(5-trifluoromethyl-1,3,4-thiadiazol-2-yl-oxy)-acetamide.

A mixing component of the formula (I) which may be particularly emphasized is the compound N-i-propyl-N-(4-fluoro-phenyl)-α-(5-trifluoromethyl-1,3,4-thiadiazol-2-yl-oxy)-acetamide (flufenacet)—hereinbelow referred to as compound (I-1).

The compounds of the formula (I) are described in the patent applications or patents mentioned above.

According to their chemical structure, the active compounds of group 2 can be assigned to the following classes of active compounds:

amides (for example beflubutamid), arylheterocycles (for example azafenidin, benzfendizone, butafenacil-allyl, cinidon-ethyl, fluazolate, flumioxazin, oxaziclomefone, profluazol, pyraflufen-ethyl, pyridatol), aryloxyphenoxypropionates (for example fenoxaprop-P-ethyl, fluazifop-P-butyl, haloxyfop-P-methyl, quizalofop-P-ethyl), carboxylic acid derivatives (for example quinclorac, triclopyr, chloroacetamides (for example dimethenamid-P, propisochlor), cyclohexanediones (for example butroxydim, clefoxydim, cycloxydim), dinitroanilines (for example benfluralin, oryzalin), imidazolinones (for example imazamox), isoxazoles (for example isoxachlortole), pyridines (for example thiazopyr), pyrimidinyl(thio)benzoates (for example pyribenzoxim, pyriftalid, pyriminobac-methyl, pyrithiobac-sodium), sulphonylureas (for example azimsulfuron, flupyrsulfuron-methyl-sodium, foramsulfuron, iodosulfuron-methyl-sodium, mesosulfuron, trifloxysulfuron, triflusulfuron-methyl), tetrazolinones (for example fentrazamide), triazoles (for example amitrole), triazolinones (for example flucarbazone-sodium, procarbazone-sodium), triazolopyrimidines (for example cloransulam-methyl, diclosulam, florasulam), triketones (for example mesotrione).

From among the active compounds of group 2, particular emphasis is given to the following mixing components:

azimsulfuron, beflubutamid, butafenacil-allyl, cinidon-ethyl, cloransulam-methyl, clefoxydim, diclosulam, fenoxaprop-P-ethyl, florasulam, flupyrsulfuron-methyl-sodium, foramsulfuron, imazamox, iodosulfuron-methyl-sodium, isoxachlortole, mesosulfuron, oxaziclomefone, procarbazone-sodium, pyriftalid, pyrithiobac-sodium, quinclorac, trifloxysulfuron.

From this group, beflubutamid is a very particularly interesting mixing component.

From this group, butafenacil-allyl is a further very particularly interesting mixing component.

From this group, cinidon-ethyl is a further very particularly interesting mixing component.

From this group, clefoxydim is a further very particularly interesting mixing component.

From this group, cloransulam-methyl is a further very particularly interesting mixing component.

From this group, diclosulam is a further very particularly interesting mixing component.

From this group, florasulam is a further very particularly interesting mixing component.

From this group, flupyrsulfuron-methyl-sodium is a further very particularly interesting mixing component.

From this group, foramsulfuron is a further very particularly interesting mixing component.

From this group, imazamox is a further very particularly interesting mixing component.

From this group, iodosulfuron-methyl-sodium is a further very particularly interesting mixing component.

From this group, isoxachlortole is a further very particularly interesting mixing component.

From this group, mesosulfuron is a further very particularly interesting mixing component.

From this group, oxaziclomefone is a further very particularly interesting mixing component.

From this group, procarbazone-sodium is a further very particularly interesting mixing component.

From this group, trifloxysulfuron is a further very particularly interesting mixing component.

The compositions according to the invention preferably comprise one or two active compounds of group 1, one to three active compounds of group 2 and optionally one active compound of group 3.

In particular, the compositions according to the invention comprise one active compound of group 1, one or two active compounds of group 2 and optionally one active compound of group 3.

Surprisingly, it has now been found that the above-defined active compound combinations of the heteroaryloxy-acetamides of the formula (I) and the above-mentioned active compounds of group 2 exhibit a particularly high herbicidal activity combined with very good crop plant compatibility and can be used for the selective control of monocotyledonous and dicotyledonous weeds in a variety of crops, in particular in barley, potatoes, maize, rice, soya beans and wheat, and additionally also for controlling monocotyledonous and dicotyledonous weeds in the semi- and non-selective field.

Surprisingly, the herbicidal activity of the active compound combinations according to the invention, of compounds of the abovementioned groups 1 and 2 exceeds the total of the actions of the individual active compounds considerably.

Thus, not just a complementation of actions but a synergistic effect is present which could not have been predicted. The novel active compound combinations are well tolerated in a variety of crops, also effecting good control of weeds which are otherwise difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges. In general, from 0.01 to 1000 parts by weight, preferably from 0.02 to 500 parts by weight and particularly preferably from 0.05 to 100 parts by weight of active compound(s) of group 2 are used per part by weight of active compound of the formula (I).

The following may be particularly emphasized as mixing components from amongst the active compounds of group 3:

1-methyl-hexyl 5-chloro-quinoline-8-oxy-acetate (cloquintocet-mexyl), ethyl 4,5-dihydro-5,5-diphenyl-3-isoxazolecarboxylate (isoxadifen-ethyl) and diethyl-1-(2,4-dichloro-phenyl)-4,5-dihydro-5-methyl-1H-pyrazole-3,5-dicarboxylate (mefenpyr-diethyl) to improve tolerance in cereals, and 4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (BAS- 145138), 4-dichloroacetyl-3,4-dihydro-3-methyl-2H-1,4-benzoxazine (benoxacor), 2,2-dichloro-N,N-di-2-propenyl-acetamide (dichlormid), 2,2-dichloro-N-(2-oxo-2-(2-propenylamino)-ethyl)-N-(2-propenyl)-acetamide (DKA-24), 3-dichloroacetyl-5-(2-furanyl)-2,2-dimethyl-oxazolidine (furilazole, MON-13900), 3-dichloroacetyl-2,2,5-trimethyl-oxazolidine (R-29148) to improve tolerance in maize.

Examples of active compound combinations according to the invention—optionally also including safeners—which may be mentioned are:

flufenacet+azimsulfuron, flufenacet+beflubutamid, flufenacet+beflubutamid+mefenpyr-diethyl, flufenacet+beflubutamid+cloquintocet-mexyl, flufenacet+butafenacil-allyl, flufenacet+cinidon-ethyl, flufenacet+clefoxydim, flufenacet+diclosulam, flufenacet+fenoxaprop-P-ethyl+mefenpyr-diethyl, flufenacet+florasulam, flufenacet+florasulam+mefenpyr-diethyl, flufenacet+florasulam+cloquintocet-mexyl, flufenacet+flupyrsulfuron-methyl-sodium, flufenacet+flupyrsulfuron-methyl-sodium+mefenpyr-diethyl, flufenacet+flupyrsulfuron-methyl-sodium+cloquintocet-mexyl, flufenacet+foramsulfuron, flufenacet+foramsulfuron+mefenpyr-diethyl, flufenacet+foramsulfuron+cloquintocet-mexyl, flufenacet+foramsulfuron+benoxacor, flufenacet+foramsulfuron+dichlormid, flufenacet+foramsulfuron+R-29148, flufenacet+foramsulfuron+AD-67, flufenacet+imazamox, flufenacet+iodosulfuron-methyl-sodium, flufenacet+iodosulfuron-methyl-sodium+mefenpyr-diethyl, flufenacet+iodosulfuron-methyl-sodium+cloquintocet-mexyl, flufenacet+isoxachlortole, flufenacet+mesosulfuron, flufenacet+oxaziclomefone, flufenacet+procarbazone-sodium, flufenacet+procarbazone-sodium+mefenpyr-diethyl, flufenacet+procarbazone-sodium+cloquintocet-mexyl, flufenacet+pyriftalid, flufenacet+pyrithiobac-sodium, flufenacet+quinclorac, flufenacet+trifloxysulfuron.

It must be considered as surprising that, from amongst a large number of known safeners or antidotes capable of antagonizing the harmful effect of a herbicide on the crop plants, it is precisely the abovementioned compounds of group 3 which are capable of almost completely compensating the harmful effect, on the crop plants, of active compounds of the formula (I) and their salts, if appropriate also in combination with one or more of the abovementioned active compounds of group 2, without adversely affecting the herbicidal efficacy towards the weeds.

Even without addition of an active compound of group 2, the following active compounds of group 3 have been found to be highly suitable according to the invention for improving the crop plant compatibility of the active compounds of the formula (I):

1-dichloroacetyl-hexahydro-3,3,8a-trimethylpyrrolo[1,2-a]-pyrimidin-6(2H)-one (dicyclonon, BAS-145138), ethyl 4,5-dihydro-5,5-diphenyl-3-isoxazolcarboxylate (isoxadifen-ethyl), diethyl 1-(2,4-dichlorophenyl)-4,5-dihydro-5-methyl-1H-pyrazole-3,5-dicarboxylate (mefenpyr-diethyl), 3-dichloroacetyl-2,2-dimethyl-oxazolidine (R-28725), 3-dichloroacetyl-2,2,5-trimethyl-oxazolidine (R-29148) and methyl 1-(2-chloro-phenyl)-5-phenyl-1H-pyrazole-3-carboxylate.

The advantageous effect of the crop plant compatibility of the active compound combinations according to the invention is likewise particularly strongly pronounced at certain concentration ratios. However, the weight ratios of the active compounds in the active combinations can be varied within relatively wide ranges. In general, from 0.001 to 1000 parts by weight, preferably from 0.01 to 100 parts by weight and particularly preferably from 0.1 to 10 parts by weight of active compound(s) of group 3 are used per part by weight of active compound of the formula (I).

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, trunks, flowers, fruiting bodies, fruits, seeds, roots, tubers and rhizomes. The plant parts also include vegetative and generative propagation material, for example cuttings, tubers, rhizomes, seedlings and seeds.

The treatment according to the invention, of the plant and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized are those which tolerate so-called ALS, 4-HPPD, EPSP and/or PPO inhibitors, such as, for example, Acuron plants.

The active compounds according to the invention can be used, for example, in the following plants:

dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium;* dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia;* monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum;* monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compound combinations according to the invention is in no way restricted to these genera, but also extends in the same manner to other plants.

The active compound combinations to be used in accordance with the invention can be employed not only in conventional cultivation methods (suitably spaced row crops), in plantation crops (for example grapevines, fruit, citrus) and in industrial plants and railtracks, on paths and squares, but also for stubble treatment and in the minimum tillage method. They are furthermore suitable as dessicants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

If the extender used is water, it is also possible to employ, for example, organic solvents as cosolvents. The following are essentially suitable as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid carriers for granules are for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are for example ligninosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The novel active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellents, growth substances, plant nutrients and soil conditioners is also possible. It may furthermore be advantageous for specific applications, in particular for the post-emergence method, to incorporate into the formulations plant-compatible mineral or vegetable oils (for example the commercial product "Oleo Dupont 11E") or ammonium salts such as, for example, ammonium sulphate or ammonium thiocyanate, as further additives.

The novel active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say by the pre- and post-emergence method. They may also be incorporated into the soil prior to sowing.

A synergistic effect in herbicides is always present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, pages 20–22, 1967):

If $X = \%$ damage by herbicide A (active compound of the formula I) at an application rate of p kg/ha and $Y = \%$ damage by herbicide B (active compound of the formula II) at an application rate of q kg/ha and E=the expected damage of herbicides A+B at an application rate of p+q kg/ha, then $$E = X + Y - (X*Y/100).$$

If the actual damage exceeds the calculated value, the combination has a superadditive effect, that is to say a synergistic effect.

The active compound combinations of the present invention do indeed have the property that their actual herbicidal activity is stronger than the calculated activity, i.e. the novel active compound combinations act synergistically.

What is claimed is:

1. A composition, comprising an herbicidally effective amount of an active compound combination consisting of (a) a heteroaryloxy-acetamide of the general formula (I)

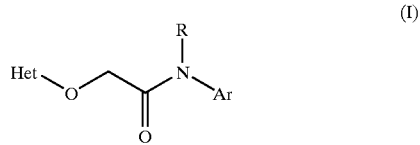

in which
Ar represents optionally halogen-, $C_1$–$C_4$-alkyl- or $C_1$–$C_4$-halogenoalkyl-substituted phenyl,
Het represents thiadiazolyl, which is substituted by halogen or by in each case optionally halogen-substituted $C_1$–$C_4$-alkyl or phenyl, and
R represents alkyl, alkenyl or alkinyl having in each case up to 4 carbon atoms,
(b) one or more herbicidally active compounds, other than the heteroaryloxy-acetamide of the formula (I), selected from the group consisting of [1,1-dimethyl-2-oxo-2-(2-propenyloxy)]ethyl 2-chloro-5-(3,6-dihydro-3-methyl-2,6-dioxo-4-trifluoromethyl-1 (2H)-pyrimidinyl)benzoate (butafenacil-allyl), ethyl 2-chloro-3-[2-chloro-5(1,3,4,5,6,7-hexahydro-1,3-dioxo-2H-isoindol-2-yl)phenyl]-2-propanoate (cinidon-ethyl), N-(2,6-difluorophenyl)-8-fluoro-5-methoxy[1,2,4]triazolo[1,5-c]pyrimidine-2-sulphonamide (florasulam), the sodium salt of 4,5-dihydro-3-methoxy-4-methyl-5-oxo-N-[(2-trifluoromethoxyphenyl)sulphonyl]-1H-1,2,4-triazole-1-carboxamide (flucarbazone-sodium), the sodium salt of N-(4,6-dimethoxy-pyrimidin-2-yl)-N'-(3-methoxycarbonyl-6trifluoromethyl-pyridin-2-yl-sulphonyl)urea (flupyrsulfuren-methyl-sodium), 2-(4-methylsulphonyl-2-nitrobenzoyl)-1,3-cyclohexanedione (mesotrione), and the sodium salt of methyl 2-[[[(4,5-dihydro-4-methyl-5-oxo-3-propoxy-1H-1,2,4-triazol-1-yl)carbonyl]amino]sulphonyl]-benzoate (procarbazone-sodium),
(c) optionally, a compound that improves crop plant tolerance selected from the group consisting of 4-dichloroacetyl-1-oxa-4-aza-spiro[4.5]decane (AD-67), 1-dichloroacetyl-hexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), α-(cyanomethoximino)phenylacetonitrile (cyometrinil), 2,2-dichloro-N-(2-oxo-2-(2-propenylamino)ethyl)-N-(2-propenyl) acetamide (DKA-24), 2,2-dichloro-N, N-di-2-propenylacetamide (dichiormid), N-(4-methylphenyl)-N'-(1-methyl-1-phenylethyl)urea (dymron), 4,6-dichloro-2-phenyl-pyrimidine (fenclorim), ethyl1-(2,4-dichlorophenyl)-5-trichloromethyl-1H-1,2,4-triazole-3-carboxylate (fenchlorazol-ethyl), phenylmethyl 2-chloro-4-trifluoro-methyl-thiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dlmethyloxazolgdine (furilazole, MON-13900), ethyl 4,5-dihydro-5,5-diphenyl-3-isoxazolecarboxylate (isoxadifen-ethyl), diethyl-1-(2,4-dichloro-phenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalene-dicarboxylic anhydride, α-(1,3dioxolan-2-yl-methoximino) phenylacetonitrile (oxabetrinil), 2,2-dichloro-N-(1,3-dioxolan-2-yl-methyl)-N-(2propenyl)acetamide (PPG-1292), 3-dichloroacetyl-2,2-dimethyl-oxazol,dine (R-28725), 3-dichloroacetyl-2,2,5-trimethyl-oxazolidine (R-29148), methyl 1-(2-chloro-phenyl)-5-phenyl-1H-pyrazole-3-carboxylate, and N-(2-methoxybenzoyl)-4-[(methylaminocarbonyl) amino] benzenesulphonamide.

2. A composition according to claim 1 wherein, in the formula (I),
Ar represents optionally fluorine-, chlorine-, bromine-, methyl-, ethyl-, or trifluoromethyl-substituted phenyl,
Het represents 1,2,4-thiadiazolyl or 1,3,4-thiadiazolyl substituted by fluorine, chlorine, bromine or by in each case optionally fluorine- and/or chlorine-substituted methyl, ethyl, n- or i-propyl, or phenyl, and
R represents methyl, ethyl, n- or i-propyl, n-, i-, s-, or t-butyl, 2-propenyl, 1-methyl-2-propenyl, 2-butenyl, 2-propynyl, 1-methyl-2-propynyl, or 2-butynyl.

3. A composition according to claim 1 wherein the heteroaryloxy-acetamide of formula (I) is N-i-propyl-N-(4-fluoro-phenyl)-α-(5-trifluoromethyl-1,3,4-thiadiazol-2-yl-oxy)acetamide.

4. composition according to claim 1 wherein the heteroaryloxy-acetamide of formula (I) is N-i-propyl-N-(4-fluoro-phenyl)-α-(5 trifluoromethyl-1,3,4-thiadiazol-2-yl-oxy)acetamide and the herbicidally active compounds of component (b) are selected from the group consisting of butafenacil-allyl, cinidon-ethyl, florasulam, flucarbazone-sodium, and procarbazone-sodium.

5. A composition according to claim 1 wherein the compounds of component (c) that improve crop plant tolerance are selected from group consisting of 1-methyl-hexyl-5-chloroquinoline-8-oxyacetate (cloquintocetmexyl), ethyl 4,5-dihydro-5,5-diphenyl-3-isoxazolecarboxylate (isoxadifen-ethyl), di-ethyl-1-(2,4-dichlorophenyl)-4,5-dihydro-5-methyl-1H-pyrazole-3,5-dicarboxylate (mefenpyr-diethyl), 4-dichloroacetyl-1-oxa-4-aza-spiro[4,5]decane (AD-67), 1-di-chloroacetyl-hexahydro-3,3,8a-trimethylpyrrolo[1,2-a]pyrimidin-6(2H)-one (BAS-145138), 4-dichloroacetyl-3,4-dihydro-3-methyl-2H-1,4-benzoxazine (benoxacor), 2,2-dichloro-N, N-di-2-propenylacetamide (dichlormid), 2,2-dichloro-N-(2-oxo-2-(2-propenylamino)ethyl)-N-(2-propenyl)acetamide (DKA-24), 3-dichloroacetyl-5-(2-furanyl)-2,2-dimethyloxazolidine (furilazole, MON-13900), and 3-dichloroacetyl-2,2,5-trimethyloxazolidine (R-29148).

6. A composition according to claim 1 wherein from 0.01 to 1000 parts by weight of the herbicidally active compounds of component (b) are used per part by weight of the heteroaryloxy-acetamide of formula (I).

7. A composition according to claim 1 wherein from 0.001 to 1000 parts by weight of one or more compounds of component (c) that improve crop plant tolerance are used per part by weight of the heteroaryloxy-acetamide of formula (I) or a mixture thereof with an herbicidally active compound of component (b).

8. A method for controlling undesirable plants comprising allowing a composition according to claim 1 to act on the undesirable plants and/or their habitat.

9. A process for preparing an herbicidal composition comprising mixing a composition according to claim 1 with surfactants and/or extenders.

* * * * *